United States Patent
Matsumoto

(10) Patent No.: US 7,560,072 B2
(45) Date of Patent: Jul. 14, 2009

(54) BLOOD ANALYZER WITH SPECIMEN CONTAINER HOLDER

(75) Inventor: Masaharu Matsumoto, Kyoto (JP)

(73) Assignee: Horiba, Ltd., Kyoto (JP)

( * ) Notice: Subject to any disclaimer, the term of this patent is extended or adjusted under 35 U.S.C. 154(b) by 325 days.

(21) Appl. No.: 11/687,817

(22) Filed: Mar. 19, 2007

(65) Prior Publication Data

US 2007/0217951 A1    Sep. 20, 2007

(30) Foreign Application Priority Data

Mar. 20, 2006    (JP) .................... P2006-075962

(51) Int. Cl.
*G01N 21/00*    (2006.01)
(52) U.S. Cl. .................... 422/67; 422/63; 422/65; 422/100; 422/101; 210/787; 210/512.1
(58) Field of Classification Search .............. 422/63, 422/65, 67, 100, 101; 210/512.1, 787
See application file for complete search history.

(56) References Cited

U.S. PATENT DOCUMENTS

| | | | |
|---|---|---|---|
| 3,614,434 A | 10/1971 | Horwitz et al. | |
| 4,475,411 A | 10/1984 | Wellerfors | |
| 5,367,157 A | 11/1994 | Nilsson et al. | |

FOREIGN PATENT DOCUMENTS

| | | |
|---|---|---|
| JP | 59-214769 | 12/1984 |
| JP | 2004-004098 | 1/2004 |

*Primary Examiner*—Jill Warden
*Assistant Examiner*—Jyoti Nagpaul

(57) ABSTRACT

A blood analyzer that can check whether a cap is in place or not and can set a mixing mode at the same time when the specimen container is inserted. A specimen container holder holds a specimen container. A holder driving part can rotatably drive the specimen container holder around an axis arranged in a generally horizontal direction. A gradient angle detecting part detects a gradient angle of the specimen container in the specimen container holder, and a control unit controls the holder driving. The control unit receives an angle detecting signal from the gradient angle detecting part, judges whether or not a blood specimen in the specimen container is to be mixed in accordance with the gradient angle and accordingly controls the holder driving part.

8 Claims, 11 Drawing Sheets

BLOOD ANALYZER WITH SPECIMEN CONTAINER HOLDER

BACKGROUND OF THE INVENTION

1. Field of the Invention

The present invention relates to a blood analyzer that analyzes a component such as red blood corpuscle, white blood corpuscle or platelet contained in a blood specimen, more specifically, to a specimen container holder on which a specimen container accommodating the blood specimen is mounted.

2. Description of Related Art

Japanese Laid Open Application No. 2004-4098 discloses a blood analyzer that can analyze a blood specimen in a specimen container without mixing the blood specimen. There is also known a blood analyzer that analyzes a blood specimen in a specimen container with mixing of the blood specimen after the specimen container, to which the blood specimen is accommodated, is set on a specimen container holder. For this type of blood analyzer, the blood specimen is mixed by tilting the specimen container to rotate, and an upper opening of the specimen container is required to be closed by a cap.

Some of the conventional blood analyzers are provided with two different kinds of specimen container holders, on one of which a specimen container, where mixing is conducted, is placed and on the other, a specimen container where mixing is not conducted, is placed.

However, these types of blood analyzers frequently may have problems such as being bulky, complicated in their mechanism, or costly because two different kinds of specimen container holders are provided. In addition, for either of the specimen container holders, a checking sensor to check whether a cap of the specimen container is secured or not is necessary. Since it is necessary for the checking sensor to identify various shapes of the cap due to differences in kinds of the specimen container, there is a problem that the blood analyzer instrument can become expensive.

In addition, some of the blood analyzers analyze a blood specimen by the use of only a specimen container whose upper opening is closed by a cap. This type of the blood analyzer is arranged so that a blood specimen is mixed on a constant basis or a user can operate the instrument to select mixing or non-mixing mode of operation.

However, a checking sensor to check whether a cap of the specimen container is placed or not is still necessary for this type of blood analyzer. In addition, there is a potential danger of an improper operation such as analyzing, without mixing the blood specimen, in an instrument that requires mixing or analyzing with mixing the blood specimen when the instrument does not require mixing due to a user's selection mistake.

Thus, there is a need to provide improvements to current blood analyzer instruments.

SUMMARY OF THE INVENTION

The present claimed invention intends to solve the above-mentioned problems and its principal object is to provide a blood analyzer of a simple arrangement that does not require a process of identifying a shape of a cap of a specimen container and that can check whether a cap is placed or not and can automatically set a mixing mode of operation when required or not at the same time when the specimen container is placed on the instrument.

More specifically, the blood analyzer includes a specimen container holder that can hold a specimen container for accommodating a blood specimen, a holder driving part that can rotatably drive the specimen container holder around an axis line arranged in a generally horizontal direction, a gradient angle detecting part that can detect a gradient angle of the specimen container arranged in the specimen container holder and a control unit that controls the holder driving part. The control unit receives an angle detecting signal from the gradient angle detecting part, judges whether the blood specimen in the specimen container is to be mixed or not in accordance with the gradient angle and controls the operation of the holder driving part.

"Mixed" here includes rotating the specimen container holder around an axis line so that an upper opening of the specimen container faces downward at least once and oscillating the specimen container without making an upper opening of the specimen container face downward.

In accordance with this arrangement, since whether the blood specimen is to be mixed or not and whether the cap is in place or not can be automatically identified by detecting the gradient angle of the specimen container, it is possible to easily identify whether the cap is in place or not. In addition, with this arrangement, it is possible to verify whether there is a cap on the specimen holder or not and to set a mixing or non-mixing mode of operation at the same time when the specimen container is set in place, thereby preventing any improper operation and eliminating any extra operation step by a user.

The control unit can comprise an angle comparing part that receives an angle detecting signal from the gradient angle detecting part and compares the gradient angle with a predetermined reference angle, and a holder controlling part that receives comparison result data from the angle comparing part and controls the holder driving part based on the comparison result data so that the specimen container is in a generally vertical state after the blood specimen in the specimen container is mixed, or controls the holder driving part based on the comparison result data without mixing the blood specimen in the specimen container so that the specimen container is in a generally vertical state.

In order to assure that a user will check whether a cap is in place or not, in the case when the user sets the specimen container, it is preferable that the reference angle is set to be an angle at which the blood specimen leaks from the specimen container accommodating a predetermined amount of the blood specimen at a time when the specimen container is tilted without closing its opening. In accordance with this arrangement, the blood specimen leaks from the specimen container at a time when the specimen container is set within an angle at which the specimen container, without a cap, is tilted to rotate so as to mix the blood specimen, thereby to urge the user to check if the cap is in place.

In addition, in order to avoid a hygiene problem such as contagion for an analyzer that deals with blood specimens, it is preferable that the blood analyzer further comprises a cover part that covers the specimen container and the specimen container holder at a time of measurement and that it accommodates any blood specimen that may leak from the specimen container.

Furthermore, in order to improve the safety features of the blood analyzer, it is preferable to include a lock mechanism to lock the cover part at an open position where the specimen container and the specimen container holder are exposed to the outside or at a closed position where the specimen container and the specimen container holder are covered by the cover part.

In addition, in order to facilitate setting the specimen container in the instrument, it is preferable to include a gradient angle adjusting mechanism that is to adjust the specimen container holder so that the specimen container is arranged at a desired angle in case of setting the specimen container on the specimen container holder.

As an embodiment of the gradient angle detecting part, it is preferable that the gradient angle detecting part uses a photo interrupter. In order to improve the convenience of the blood analyzer, it is preferable that the specimen container holder be capable of holding various different kinds of specimen containers.

As mentioned above, in accordance with this invention, since whether the blood specimen is to be mixed or not and whether the cap is in place or not is identified by detecting the gradient angle of the specimen container, it is possible to easily identify whether there is a cap or not. In addition, with this arrangement, it is possible to automatically verify whether there is a cap on the specimen holder or not and to set a mixing or non-mixing mode of operation at the same time when the specimen container is set, thereby to minimize any possible improper operation associated with an extra operation by a user.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

Reference will now be made in detail to the preferred embodiments of the invention which set forth the best modes contemplated to carry out the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well known methods, procedures, components, and circuits have not been described in detail as not to unnecessarily obscure aspects of the present invention.

Embodiments in accordance with a blood analyzer of the present claimed invention will be described with reference to the accompanying drawings.

The blood analyzer 1 in accordance with a first embodiment measures the WBC (a number of white blood corpuscles), the RBC (a number of red blood corpuscles), the PLT (a number of platelets), the MCV (a volume of red blood corpuscle) and the Hct (a hematocrit value) by the use of an electric resistance measurement and also measures the Hgb (a hemoglobin concentration) by the use of an absorptiometric method in a cyanmethemoglobin method (makes a CBC measurement).

Figure 1:
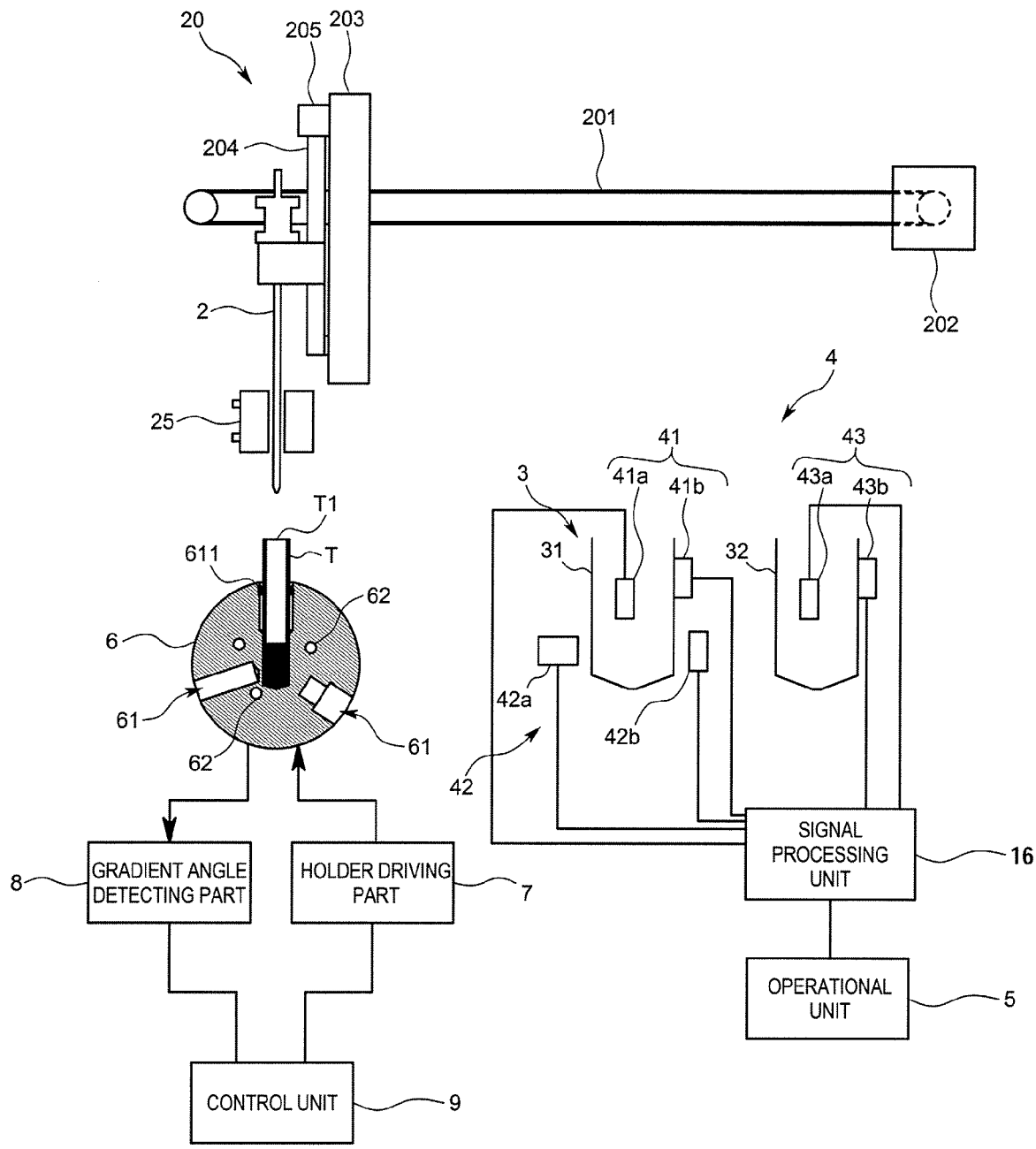
FIG. 1 is a configuration pattern diagram showing one embodiment in accordance with a blood analyzer of the present claimed invention.

A basic configuration of the blood analyzer 1 comprises, as shown in FIG. 1, a sampling nozzle 2 that sucks a blood specimen from a specimen container T, a measuring cell 3 that accommodates the blood specimen sucked by the sampling nozzle 2 and a diluent solution to measure the blood specimen, a blood measuring part 4 that measures the blood specimen in the measuring cell 3, and an operational unit 5 that analyzes the WBC of the blood specimen by receiving the measured data from the blood measuring part 4 through a signal processing unit 16.

Figure 7:
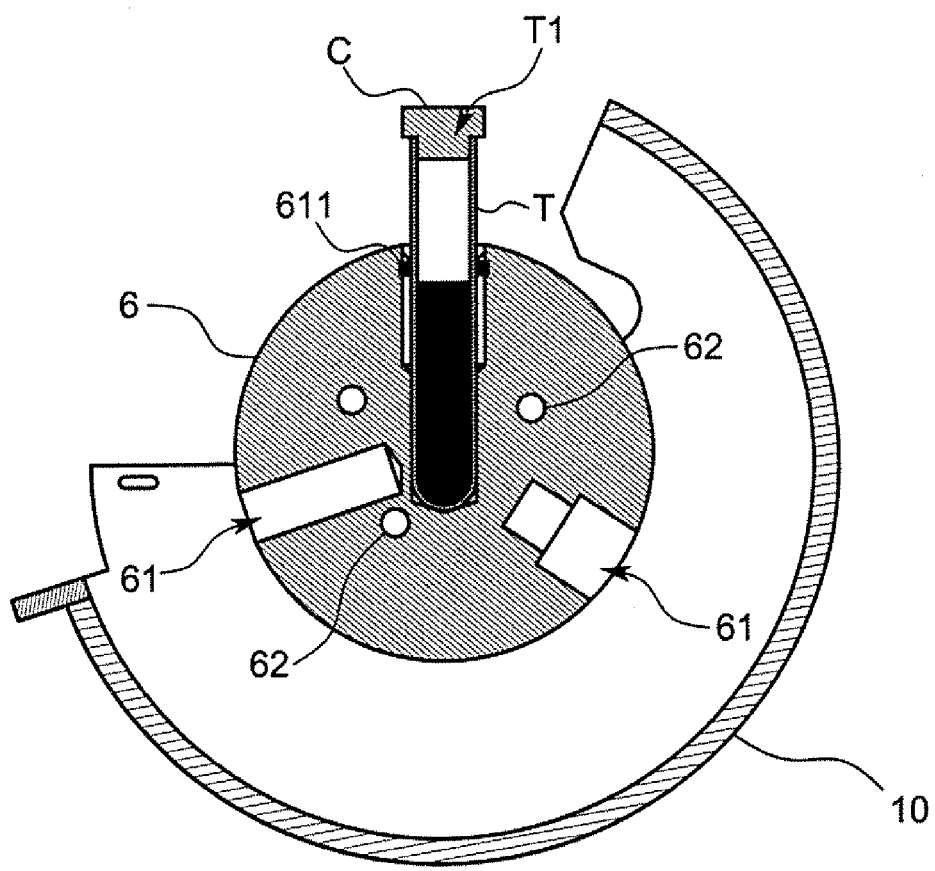
FIG. 7 is a view showing the specimen container holder and a cover part located at an open position in accordance with this embodiment.

In this embodiment the specimen container T is in a shape of a cylinder or tube made of a resin such as a transparent plastic and has an opening T1 in its upper portion. The opening T1 is covered by, for example, a cap C, as shown in FIG. 7, also made of resin in case of accommodating a blood specimen in which mixing is to be conducted.

The sampling nozzle 2 sucks or discharges the blood specimen in the specimen container T when held in a generally vertical state. The sampling nozzle 2 is driven by a nozzle driving part 20 to be described later. In FIG. 1 a nozzle retrojector 25 is used to wash an outer peripheral face or surface of a distal end portion of the sampling nozzle 2.

The nozzle driving part 20 comprises a first timing belt 201 arranged in a horizontal direction, a motor 202 to drive the first timing belt 201, a housing 203 that is fixed to the first timing belt 201 and that can make a reciprocating motion in a horizontal direction, a second timing belt 204 arranged in the housing 203 vertically, and a motor 205 to drive the second timing belt 204. The sampling nozzle 2 is mounted on the second timing belt 204 and can be moved horizontally by the first timing belt 201 and vertically by the second timing belt 204.

The measuring cell 3 comprises a WBC/Hgb measuring cell 31 (hereinafter to be called as just "a WBC cell") to measure the WBC (a number of white blood corpuscles) and the Hgb (a Hemoglobin concentration), and a RBC/PLT measuring cell 32 (hereinafter to be called as just a RBC cell) to measure the RBC (a number of red blood corpuscles) and the PLT (a number of platelets).

The blood specimen is filled into the WBC cell 31 through the sampling nozzle 2 and primarily diluted with a diluent solution from a diluent solution container (not shown in the drawings), and then a hemolyzing agent from a hemolyzing agent container (not shown in drawings) is filled into the WBC cell 31. After this, the WBC and the Hgb are measured. The primarily diluted blood specimen is filled in the RBC cell 32 through the sampling nozzle 2 and then secondarily diluted with a diluent solution from the diluent solution container (not shown in drawings). After this, the RBC and the PLT are measured.

The blood measuring part 4 comprises a WBC measuring part 41, an Hgb measuring part 42 and a RBC/PLT measuring part 43. The WBC measuring part 41 measures the WBC by the use of measuring electrodes 41a, 41b such as platinum electrodes arranged in the WBC cell 31. The Hgb measuring part 42 measures the Hgb by the use of a light source 42a such as, for example, a halogen lamp arranged outside of the WBC cell 31 and a light detector 42b that detects light transmitting through the WBC cell 31. The RBC/PLT measuring part 43 measures the RBC/PLT by the use of measuring electrodes 43a, 43b such as, for example, platinum electrodes.

The operational unit 5 receives measured data from the blood measuring part 4, conducts a predetermined operation and analyzes the WBC, the RBC, the PLT, the MCV, the Hct of the blood specimen in the measuring cell 3.

The blood analyzer 1 of this embodiment comprises, as shown in FIG. 1, a specimen container holder 6 that holds the specimen container T, a holder driving part 7 that rotatably drives the specimen container holder 6 around an axis line arranged in a generally horizontal direction, a gradient angle detecting part 8 that detects a gradient angle $\theta_I$ of the specimen container T arranged on the specimen container holder 6 from a vertical state, and a control unit 9 that controls the holder driving part 7.

Each portion of the blood analyzer 1 will now be explained.

The specimen container holder 6 can be of a disk-shape and holds the specimen container T, and has a mounting hole 61 to mount and hold the specimen container T and a detecting opening 62 to detect the gradient angle $\theta_I$ of the specimen container T from the vertical state.

The mounting hole 61 extends toward a radial direction so as to expose its opening T1 to a side surrounding face of the specimen container holder 6. A fixing part 611 is arranged on an inner wall part of the mounting hole 61 to push and fix the specimen container T to the mounting hole 61. The fixing part 611 is, for example, an O-ring. In this embodiment, three mounting hole 61 are arranged so as to make it possible to hold three different shapes of the container.

The detecting opening 62 is to detect the gradient angle $\theta_I$ of the specimen container T by the use of an optical transparent photo interrupter, to be described later, and to discriminate a vertical state of the specimen container T, a state of the specimen container T tilted within a predetermined range for an angle wherein mixing does not occur (non-mixing angle), and a state of the specimen container T tilted within a range of an angle wherein mixing does occur (mixing angle).

The specimen container holder 6 of this embodiment can be arranged to be rotatable manually by a user. More specifically, the specimen container holder 6 is rotatable to facilitate selecting one of the three mounting holes 61 and determining the gradient angle $\theta_I$ of the specimen container T to be mounted on the mounting hole 61. A gradient angle adjusting mechanism A is arranged in order to facilitate a rotational operation of the specimen container holder 6.

Figure 2:
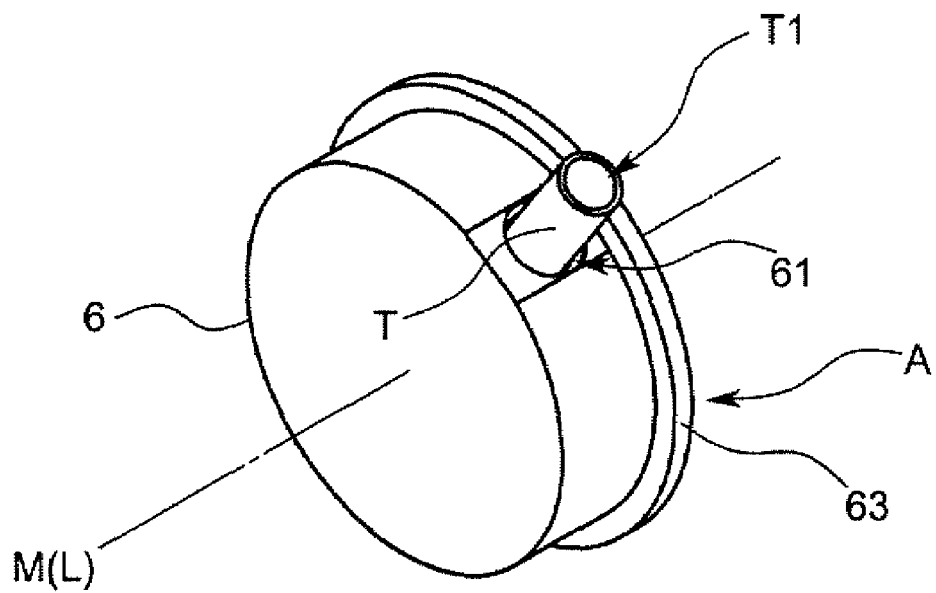
FIG. 2 is a perspective view of a specimen container holder in accordance with this embodiment.

The gradient angle adjusting mechanism A can adjust the specimen container holder 6 so that the specimen container T is placed at a desired gradient angle $\theta_I$ at a time when the specimen container T is set on the specimen container holder 6. In this embodiment, the gradient angle adjusting mechanism A is, as shown in FIG. 2, a flange part 63 arranged on the side surrounding face of the specimen container holder 6. With this arrangement, it is possible for a user to manually rotate the predetermined mounting hole 61 to be within an angle range wherein the blood specimen is mixed because the specimen container T is tilted to rotate (a mixing angle range) and an angle range wherein the blood specimen is not mixed even though the specimen container T is tilted (a non-mixing angle range). Furthermore, in this embodiment, in order to facilitate setting the gradient angle $\theta_I$ of the specimen container T, a click stop feeling is created at a predetermined angle within the mixing angle range and at a predetermined angle within the non-mixing angle range by making use of a click stop mechanism. That is a cam and follower detent arrangement can be used.

The holder driving part 7 drives the specimen container holder 6 to rotate around an axial line (hereinafter called as a rotational axis line L) that is arranged in a generally horizontal direction. In other words, the holder driving part 7 drives the specimen container holder 6 to rotate on a generally vertical plane. The holder driving part 7 comprises a motor arranged on a body of the blood analyzer 1 and a transmission gear that transmits a rotational movement of the motor to the specimen container holder 6, and the motor is controlled by a holder controlling part 93 of the control unit 9, to be described later. In this embodiment, the rotational axis line L coincides with a center axis line M of the specimen container holder 6. Furthermore, a center axis line N of the specimen container T mounted on the specimen container holder 6 is arranged to cross the center axis line M of the specimen container holder 6.

The gradient angle detecting part 8 detects the gradient angle $\theta_I$ of the specimen container T arranged on the specimen container holder 6 relative to a vertical state of the specimen container T, and uses LEDs as a light source and an optical transparent photo interruptor that makes use of a photo transistor as a photodetector. More specifically, the LEDs and the photo transistor are separately arranged to face each other on both sides of the specimen container holder 6 and detect the gradient angle $\theta_I$ by making use of a relationship to the detecting opening 62 arranged on the specimen container holder 6.

Figure 3:
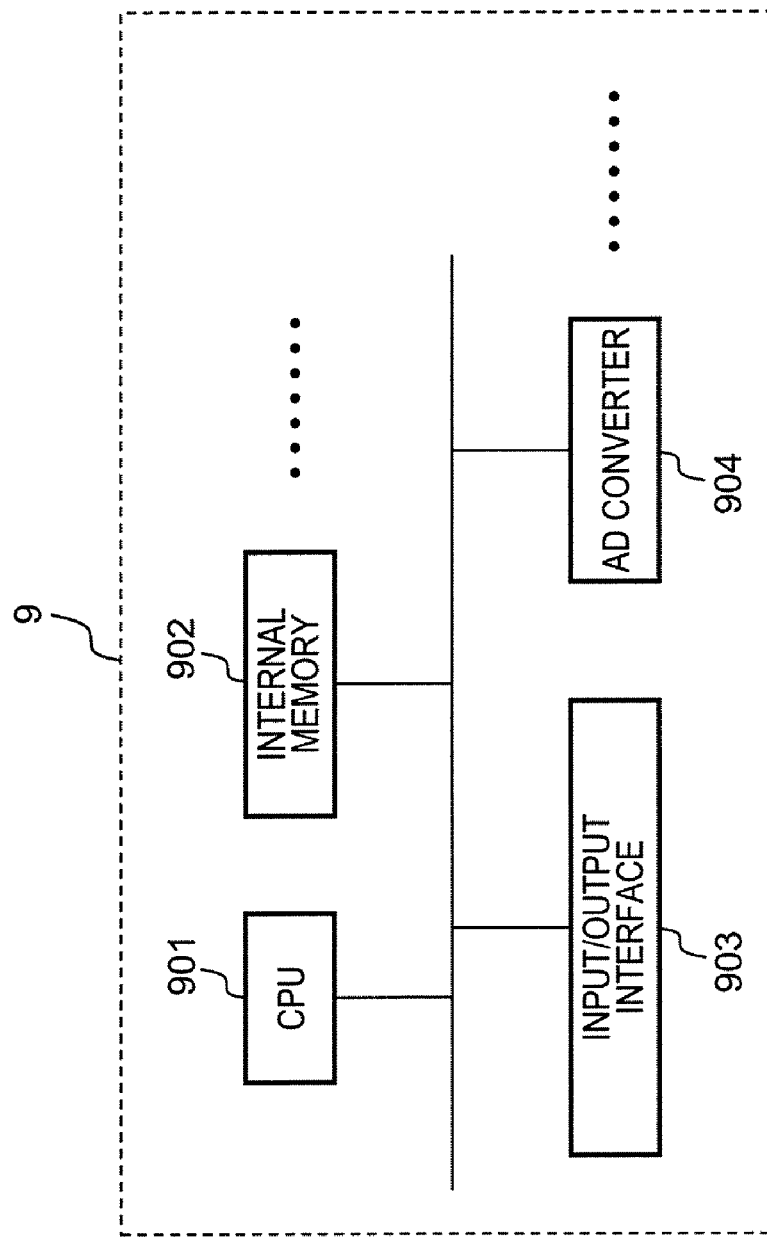
FIG. 3 is a configuration diagram of a control unit in accordance with this embodiment.
Figure 4:
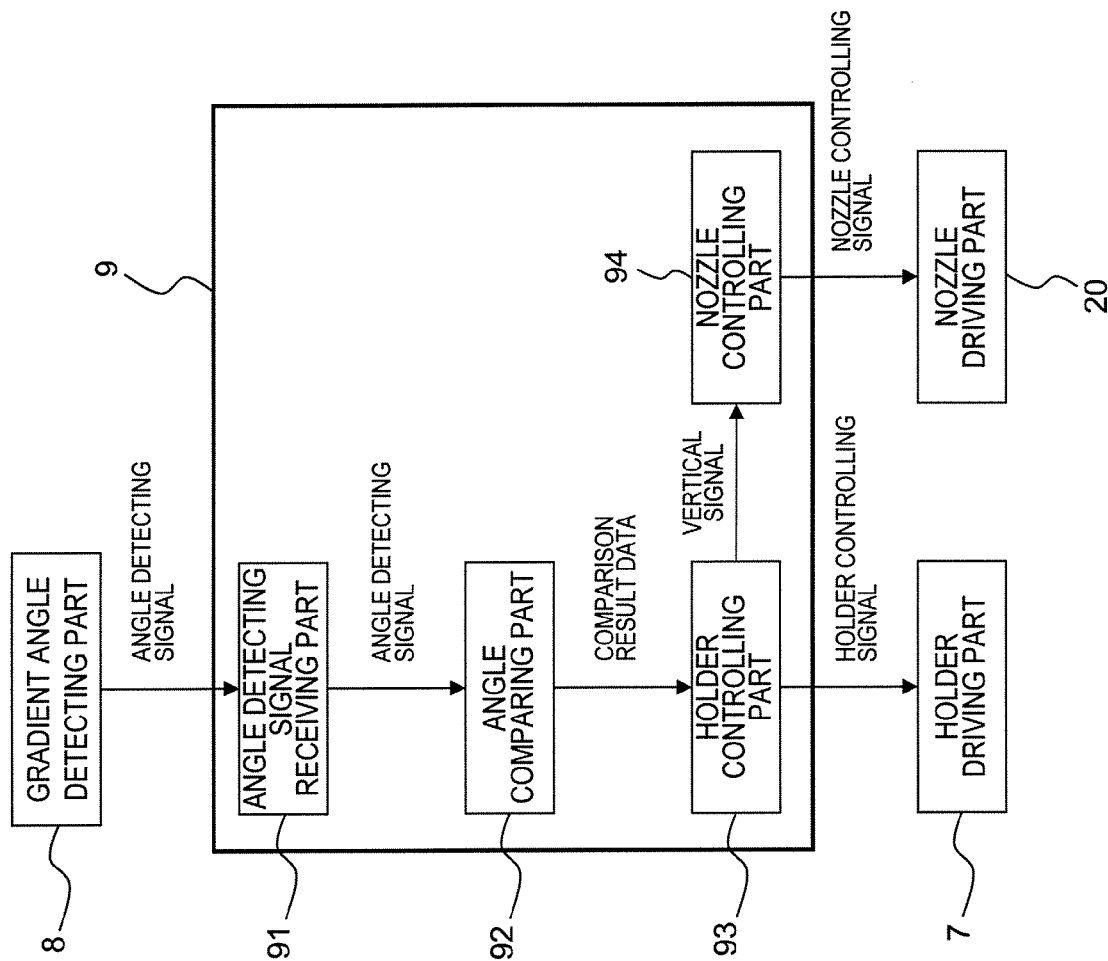
FIG. 4 is a functional diagram of the control unit in accordance with this embodiment.

The control unit 9 controls the holder driving part 7 based on an angle detecting signal from the gradient angle detecting part 8. The configuration diagram of the control unit 9 is shown in FIG. 3. The control unit 9 is a general purpose or an exclusive use computer comprising a CPU 901, an internal memory 902, an input/output interface 903, and an AD converter 904, and functions, as shown in FIG. 4, as an angle detecting signal receiving part 91, an angle comparing part 92, a holder controlling part 93 and a nozzle controlling part 94 by operating the CPU 901 and its peripheral devices based on a program stored in a predetermined area of the internal memory 902.

Each part of the control unit will be described in detail.

The angle detecting signal receiving part 91 receives a gradient angle detecting signal from the gradient angle detecting part 8 and outputs it to the angle comparing part 92.

The angle comparing part 92 receives the gradient angle detecting signal output by the angle detecting signal receiving part 91, compares the gradient angle $\theta_I$ of the specimen container T with a previously determined reference angle $\theta_B$ and outputs the comparison result data to the holder controlling part 93.

Figure 5:
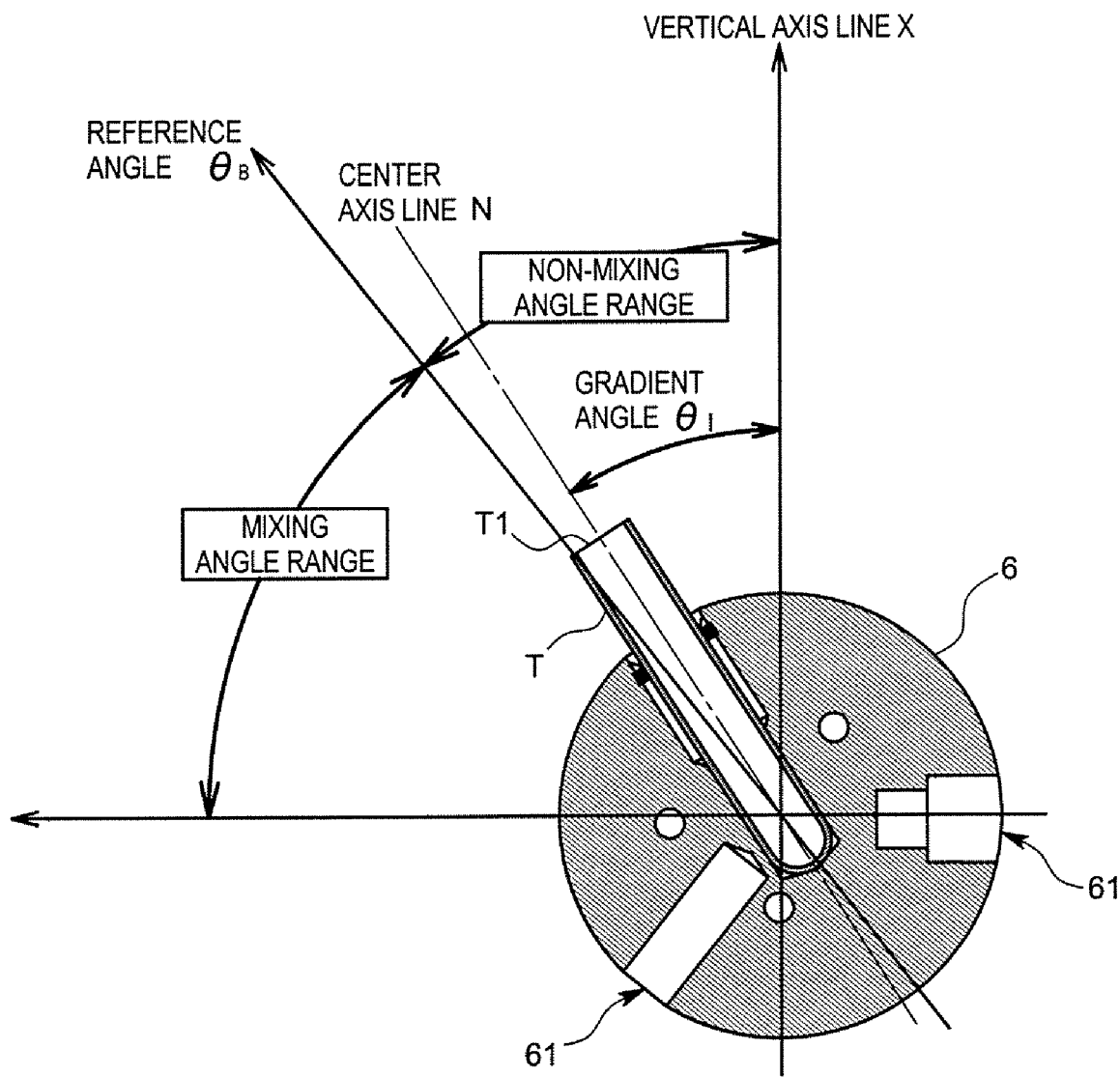
FIG. 5 is a view showing a gradient angle of a specimen container and a reference angle in accordance with this embodiment.

The gradient angle $\theta_I$ is, as shown in FIG. 5, an angle between the center axis line N (a vertical axis line X) of the specimen container T in a vertical state and the center axis line N of the specimen container T in a tilted state.

In addition, the previously determined reference angle $\theta_B$ is set to be an angle at which the blood specimen will leak from the specimen container T accommodating a predetermined amount of the blood specimen at a time when the specimen container T is tilted without closing its opening T1. More specifically, if the specimen container T accommodating a predetermined amount of the blood specimen is tilted at a gradient angle $\theta_I$ that is within the mixing angle range without closing the opening T1, the blood specimen leaks from the opening T1 of the specimen container T. This makes it possible for a user to check whether a cap is properly placed or not when the user sets the specimen container T in the holder 6.

Figure 6:
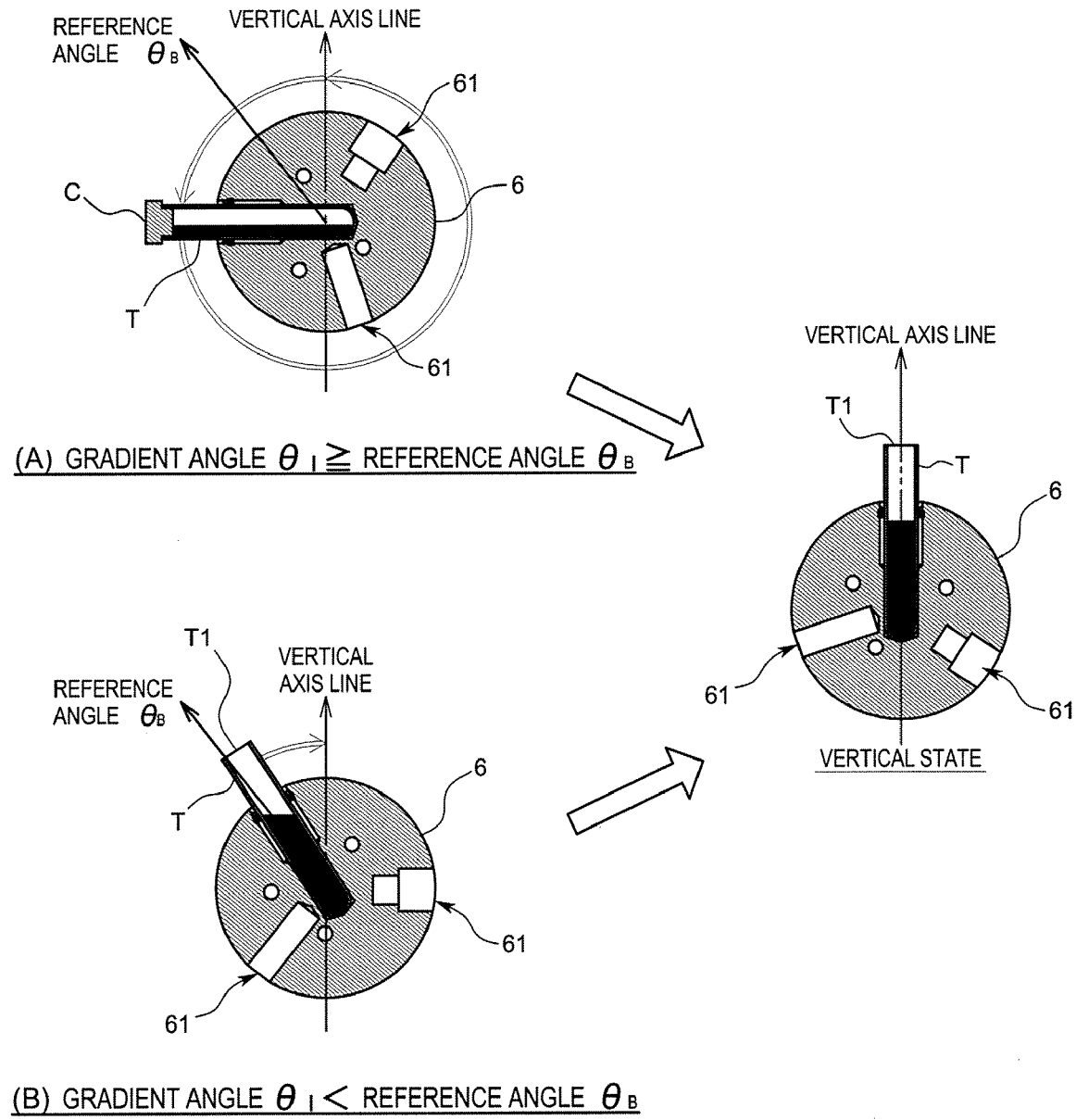
FIG. 6 is a view showing an operation of the specimen container holder in accordance with this embodiment.

The holder controlling part 93 receives the comparison result data from the angle comparing part 92 and controls the holder driving part 7 based on the comparison result data. More specifically, in case that the gradient angle $\theta_I$ of the specimen container T is bigger than the reference angle $\theta_B$, the holder controlling part 93 tilts the specimen container T to rotate so as to mix the blood specimen in the specimen container T and controls the holder driving part 7 so that the specimen container T is in a generally vertical state as shown in FIG. 6(A). In case that the gradient angle $\theta_I$ of the specimen container T is smaller than the reference angle $\theta_B$, the holder controlling part 93 controls the holder driving part 7 so that the specimen container T is in a generally vertical state without tilting the specimen container T as shown in FIG. 6(B). Each arrow in FIGS. 6(A) and (B) shows a direction to rotate the specimen container T.

At this time, to tilt the specimen container T to rotate so as to mix the blood specimen in the specimen container T means to mix the blood specimen by rotating the specimen container holder 6 so that the upper opening T1 of the specimen container T faces downward (a headfirst state) at least once.

The nozzle controlling part 94 controls the nozzle driving part 20 in order to make the sampling nozzle 2 conduct a predetermined operation in a state that the holder controlling part 93 terminates rotation control of the specimen container holder 6 and the specimen container holder 6 holds the specimen container T in a generally vertical state.

In addition to the above-mentioned arrangement, the blood analyzer 1 of this embodiment comprises a cover part 10 that covers the specimen container T and the specimen container holder 6 at a time of measurement and that accommodates the blood specimen leaking from the specimen container T and a lock mechanism that locks the cover part 10 at a predetermined position.

The cover part 10, shown in FIG. 7, covers the specimen container T and the specimen container holder 6 at a time of measurement and accommodates any blood specimen leaking from the specimen container T. More concretely, the cover part 10 is attached to a casing (not shown in drawings) of the blood analyzer 1 in a rotatable manner between an open position where the specimen container T and the specimen container holder 6 are exposed to the outside and a closed position where the specimen container T and the specimen container holder 6 are covered. The cover part 10 is so arranged that if the blood specimen leaks from the specimen container T, the spilled blood specimen can be accommodated at both an open position and a closed position.

The lock mechanism locks the cover part 10 so as not to rotate at a time when the cover part 10 is located at the open position and the closed position and, for example, a latching mechanism can be used as the lock mechanism. As a concrete operation, the latching mechanism (not shown in drawings) is arranged on the casing and the cover part 10 locks the cover part 10 so as not to rotate at a time when the cover part 10 is located at both the open position and the closed position.

Figure 8:
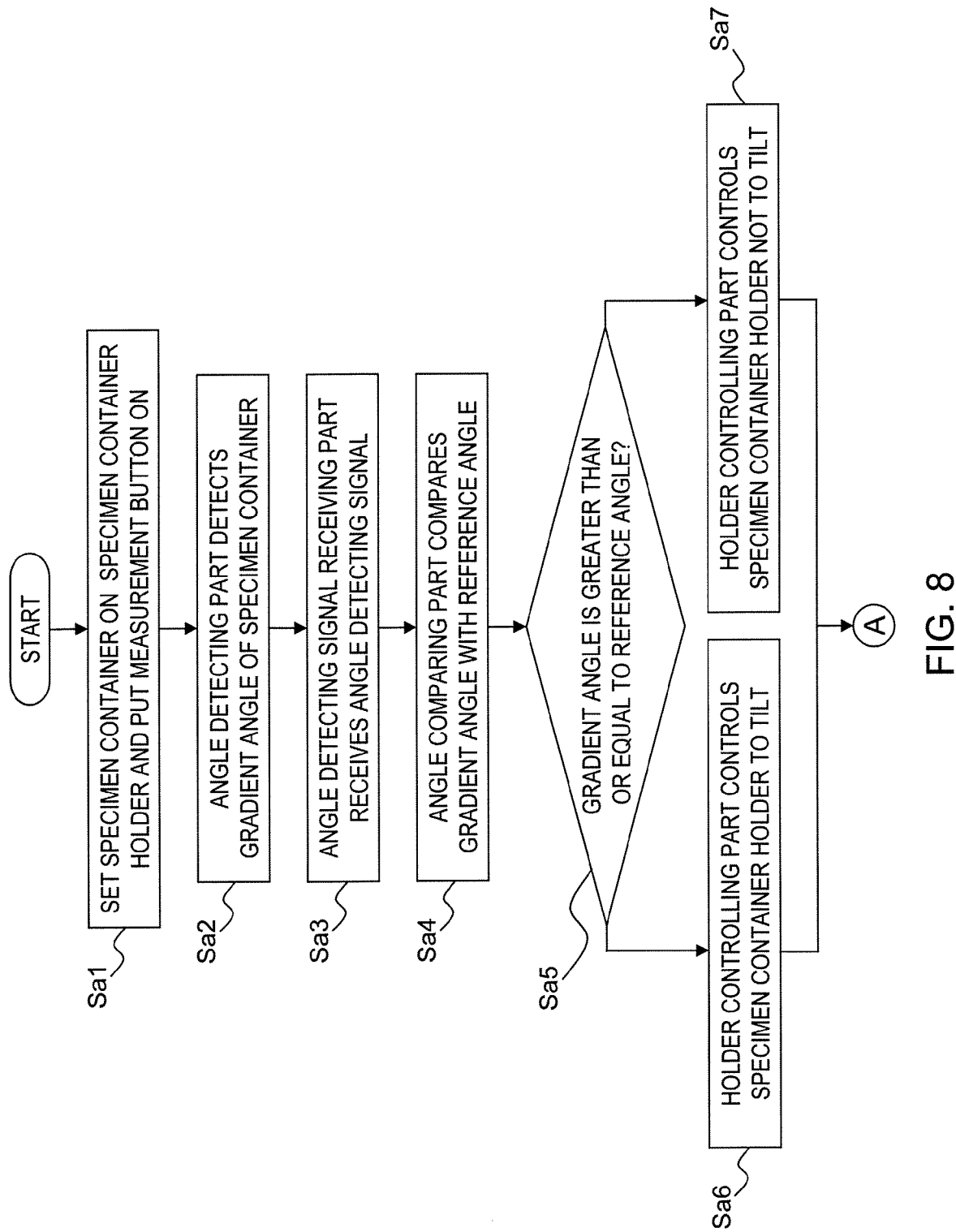
FIG. 8 is an operation flow chart mainly showing an operation of the specimen container holder of the blood analyzer in accordance with this embodiment.
Figure 9:
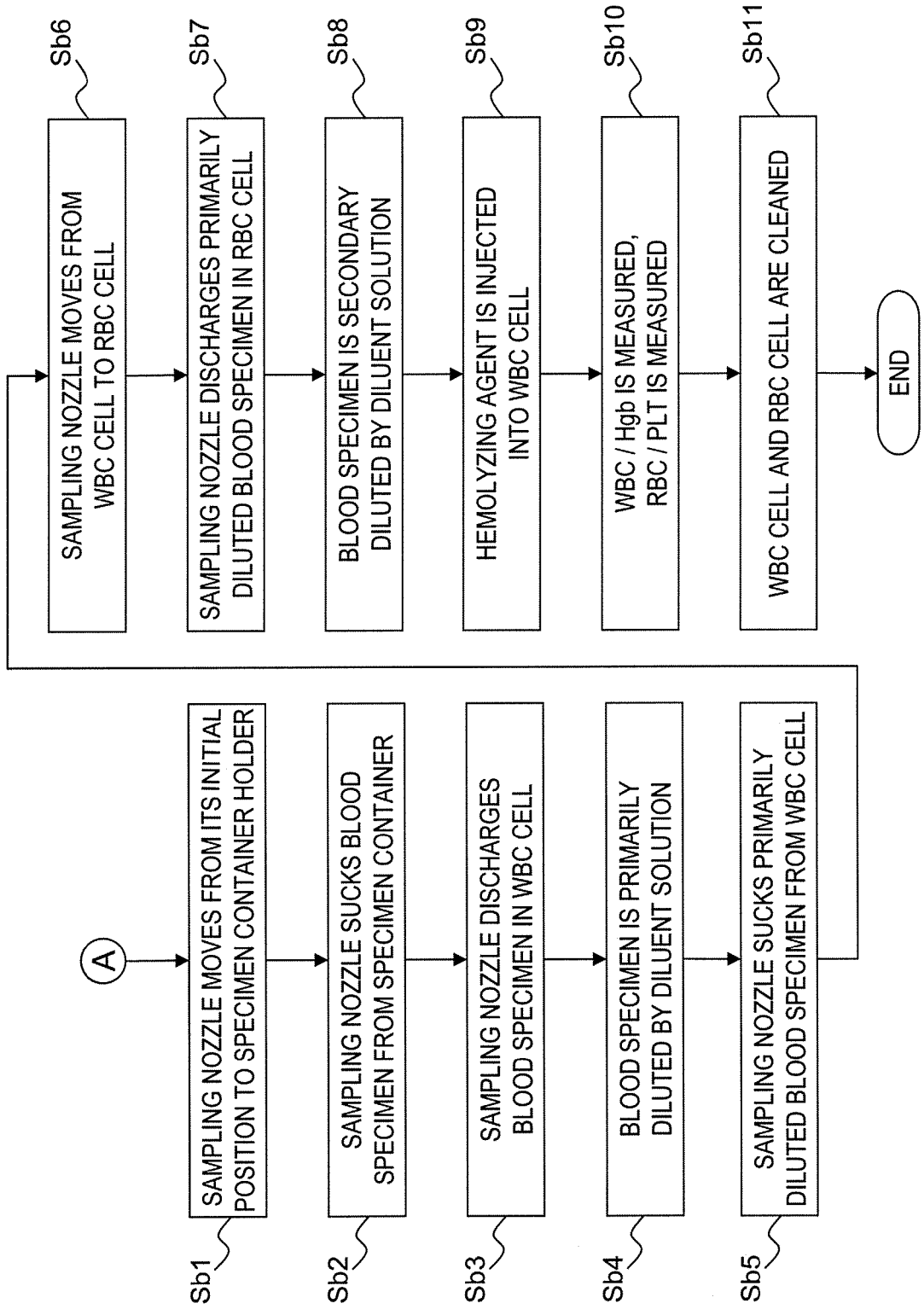
FIG. 9 is an operation flow chart showing a measurement operation of the blood analyzer in accordance with this embodiment of the invention.

Next, an operation of the blood analyzer 1 with the above arrangement will be explained with reference to the flow charts in FIG. 8 and FIG. 9.

First, mainly an operation of the specimen container holder 6 will be explained with reference to FIG. 8. A user manually rotates the specimen container holder 6 by making use of the gradient angle adjusting mechanism A at a time of setting the specimen container T that accommodates the blood specimen, sets the mounting hole 61 that fits to a kind of the specimen container T at a desired gradient angle $\theta_I$ and inserts the specimen container T into the mounting hole 61.

Next, the user rotates the cover part 10 from an open position to locate the cover part 10 at the closed position so as to block the specimen container T and the specimen container holder 6 from outside contact. Later the user pushes a measurement button (not shown in the drawings) to an ON position (Step Sa1). Then the gradient angle detecting part 8 detects the gradient angle $\theta_I$ of the specimen container T (Step Sa2), and the angle detecting signal receiving part 91 receives the gradient angle detecting signal (Step Sa3) and outputs it to the angle comparing part 92. Then the angle comparing part 92 compares the gradient angle $\theta_I$ with the reference angle $\theta_B$ (Step Sa4), judges whether or not the gradient angle $\theta_I$ is greater than or equal to the reference angle $\theta_B$, and outputs the comparison result data to the holder controlling part 93 (Step Sa5).

Based on the comparison result data, the holder controlling part 93 controls the holder driving part 7 to tilt the specimen container T so as to be in a generally vertical state by rotating the specimen container T to mix the blood specimen in the specimen container T in the case that the gradient angle $\theta_I$ of the specimen container T is bigger than or equal to the reference angle $\theta_B$ (Step Sa6). In the case that the gradient angle $\theta_I$ is smaller than the reference angle $\theta_B$, the holder controlling part 93 controls the holder driving part 7 so as to hold the specimen container T in a generally vertical state without tilting the specimen container T during rotation (Step Sa7).

After the above-mentioned operation, the sampling nozzle 2 located at an initial position moves to the upside of the specimen container T held in the vertical state by the specimen container holder 6 (Step Sb1), and sucks the blood specimen (whole blood) in the specimen container T (Step Sb2). After this, the sampling nozzle 2 moves to a position of the WBC cell 31 and discharges the blood specimen in the WBC cell 31 (Step Sb3). At the same time, a predetermined amount of a diluent solution in the diluent solution container 11 is filled into the WBC cell 31 so as to conduct a primary dilution for the blood specimen (Step Sb4).

The sampling nozzle 2 located at the position of the WBC cell 31 sucks a predetermined amount of the blood specimen to which the primary dilution has been conducted (Step Sb5), moves to a position of the RBC cell 32 (Step Sb6), and discharges the blood specimen to which the primary dilution has been conducted to the RBC cell 32 (Step Sb7). Then a predetermined amount of the diluent solution in the diluent solution container 11 is filled into the RBC cell 32 and a secondary dilution is conducted for the blood specimen (Step Sb8).

After the primary dilution and the secondary dilution, a predetermined amount of hemolyzing agent in the hemolyzing agent container 12 is filled into the WBC cell 31 (Step Sb9), and then the WBC and the Hgb are measured. The RBC and the PLT are also measured in the RBC cell 32, and then the measured data is output to the operational unit 5 through a signal processing unit (Step Sb10).

The operational unit 5 calculates the WBC, the RBC, the PLT, the MCV and the Hct based on the measured data from the blood measuring part 4.

After the measurement, the blood specimen to which the primary dilution has been conducted and the blood specimen to which the secondary dilution has been conducted are discharged from the measuring cell 3 to a waste solution container and the WBC cell 31 and the RBC cell 32 are washed by the diluent solution and cleaning solvent from a cleaning solvent container (Step Sb11).

With the blood analyzer 1 in accordance with this embodiment of the above-mentioned arrangement, whether mixing of the blood specimen is conducted or not and whether a cap C is placed or not are recognized by detecting the gradient angle $\theta_T$ of the specimen container T. As a result of this, it is possible to deal with almost all shapes of caps and containers of the commonly used specimen container T and it becomes easy to check whether the cap C is in place or not. In addition, since an operation of setting the specimen container T also functions as an operation of selecting mixing/non-mixing and an operation of checking whether the cap C is in place or not, it is possible to prevent an operational error associated with an excess operation by a user and to urge the user to check whether or not the cap C is in place.

In addition, since the reference angle $\theta_B$ is set at an angle in which the blood specimen will leak from the opening T1 of the specimen container T at a time when the specimen container T accommodating the predetermined amount of the blood specimen is tilted without closing the opening T1, the blood specimen leaks at a time when the specimen container T without the cap C is set at the mixing angle, thereby to urge the user to check whether or not the cap C has been properly put in place.

The present claimed invention is not limited to the above-mentioned embodiment.

Figure 10:
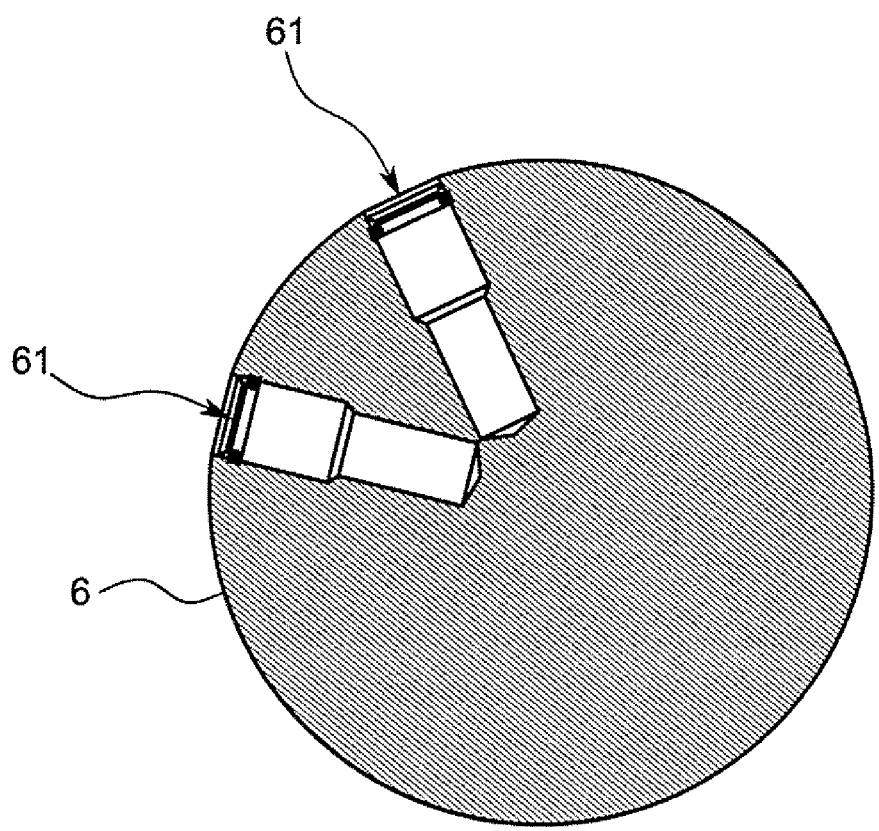
FIG. 10 is a cross-sectional view of the specimen container holder in accordance with one modified embodiment of the invention.

For example, as shown in FIG. 10, two mounting holes 61, 61 with different angles to set a specimen container may be arranged on a specimen container holder 6 so that a user can recognize mixing or non-mixing without a manual operation of rotating the specimen container holder 6 by checking the mounting hole 61 into which the specimen container is inserted.

Figure 11:
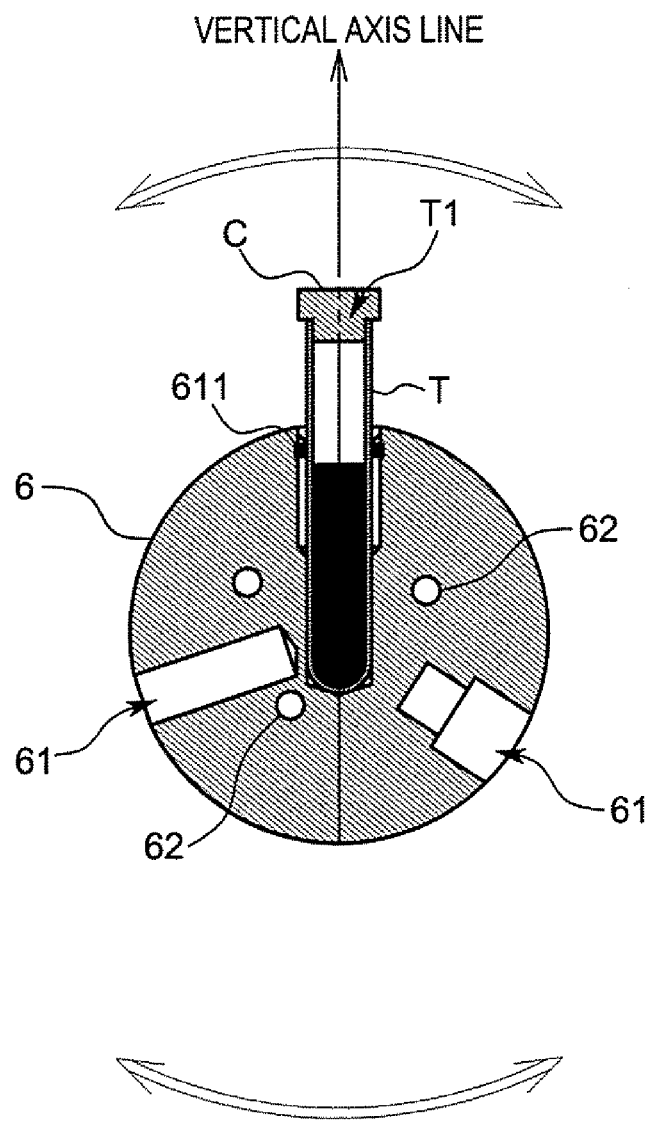
FIG. 11 is a view showing an operation of a specimen container holder in accordance with another modified embodiment.

In addition, the blood specimen is mixed with the operation of rotating the specimen container so that the upper opening of the specimen container faces downward at least once in the above-mentioned embodiment, however, the blood specimen may be mixed with an operation of just oscillating the specimen container without making the upper opening of the specimen container face downward as shown in FIG. 11.

Furthermore, the gradient angle is based on a vertical state of the specimen container in the above-mentioned embodiment, however, the gradient angle may be based on a horizontal state, a state at a reference angle or a state of being tilted at a predetermined angle. More specifically, the angle detecting part may detect a gradient angle from the horizontal state, a gradient angle from a state at the reference angle or a gradient angle from a state of being tilted at a predetermined angle. If the angle detecting part detects the gradient angle from the state at the reference angle, it is possible to determine mixing or non-mixing by just detecting the gradient angle without making a comparison.

If the angle detecting part detects, for example, the gradient angle from the horizontal state, the holder controlling part controls the holder driving part as follows. More specifically, in case that the gradient angle from the horizontal state is smaller than the reference angle when the comparison result data is received from the angle comparing part, the holder controlling part tilts the specimen container to rotate so as to mix the blood specimen in the specimen container and controls the holder driving part so that the specimen container is in a generally vertical state. In case that the gradient angle is bigger than the reference angle, the holder controlling part controls the holder driving part so that the specimen container is in a generally vertical state without tilting the specimen container to rotate so as to mix the blood specimen in the specimen container.

In addition, the specimen container holder into which the specimen container can be inserted from any direction may be used.

Furthermore, the gradient angle detecting part uses the optical transparent photo interrupter in the above-mentioned embodiment, however, the gradient angle detecting part may use an optical reflection photo interrupter or a rotary encoder.

In addition, the specimen container holder is disk-shaped in the above-mentioned embodiment, however, the specimen container may have a different shape to grasp the specimen container.

Furthermore, the gradient angle detecting part detects the gradient angle of the specimen container after the measurement button is put in the ON position in the above-mentioned embodiment, however, it is not limited to this mode and the gradient angle may be detected at a time of inserting the specimen container into a mounting hole of the specimen container holder or at a time when the specimen container and the specimen container holder are blocked from outside by the cover part.

In addition to the above, the lock mechanism uses the latch mechanism in the above-mentioned embodiment, however the lock mechanism may use a solenoid. An arrangement of the lock mechanism using the solenoid comprises, for example, a fixing rod to be inserted into an engaging opening 101 arranged on the cover part 10 and a fixing rod driving part that detachably mounts the fixing rod on the engaging opening 101. The fixing rod driving part drives the fixing rod to be inserted into the engaging opening 101 in case of fixing the cover part 10, and drives the fixing rod to be pulled out of the engaging opening 101 in case of not fixing the cover part 10.

The operational unit that analyzes the blood specimen and the control unit that controls the specimen container holder are separately arranged in the above-mentioned embodiment, however a single information processing unit may both analyze the blood specimen and control the specimen container holder.

In addition, a part or all of the above-mentioned embodiment or the modified embodiment may be arbitrarily combined, and it is a matter of course that the present claimed invention is not limited to the above-mentioned embodiment and may be variously modified without departing from the spirit of the invention.

Those skilled in the art will appreciate that various adaptations and modifications of the just-described preferred embodiment can be configured without departing from the scope and spirit of the invention. Therefore, it is to be understood that, within the scope of the amended claims, the invention may be practiced other than as specifically described herein.

What is claimed is:

1. A blood analyzer comprising;
   a specimen container holder that holds a specimen container accommodating a blood specimen,
   a holder driving part that rotatably drives the specimen container holder around an axis line arranged in a generally horizontal direction;
   a gradient angle detecting part that detects a gradient angle of the specimen container arranged in the specimen container holder; and
   a control unit that controls the holder driving part, wherein the control unit receives an angle detecting signal from the gradient angle detecting part, judges whether the blood specimen in the specimen container is to be mixed or not in accordance with the gradient angle and controls the holder driving part.

2. The blood analyzer described in claim 1, wherein the control unit comprises
   an angle comparing part that receives the angle detecting signal from the gradient angle detecting part and compares the gradient angle with a predetermined reference angle, and
   a holder controlling part that receives comparison result data from the angle comparing part and controls the holder driving part based on the comparison result data so that the specimen container is in a generally vertical state after the blood specimen in the specimen container is mixed, or controls the holder driving part based on the comparison result data without mixing the blood specimen in the specimen container so that the specimen container is in a generally vertical state.

3. The blood analyzer described in claim 2, wherein the reference angle is set at an angle at which the blood specimen will leak from the specimen container accommodating a predetermined amount of the blood specimen at a time when the specimen container is tilted without closing its opening.

4. The blood analyzer described in claim 1 wherein further comprising a cover part that covers the specimen container and the specimen container holder at a time of measurement and that retains any blood specimen leaking from the specimen container.

5. The blood analyzer described in claim 1 wherein comprising a lock mechanism that locks the cover part at an open position where the specimen container and the specimen container holder are exposed to the outside or at a closed position where the specimen container and the specimen container holder are covered by the cover part.

6. The blood analyzer described in claim 1 wherein comprising a gradient angle adjusting mechanism to adjust the specimen container holder so that the specimen container is arranged at a predetermined angle for setting the specimen container on the specimen container holder.

7. The blood analyzer described in claim 1 wherein the gradient angle detecting part uses a photo interrupter.

8. The blood analyzer described in claim 1 wherein the specimen container holder is configured to hold different configurations of specimen containers.

* * * * *